(12) United States Patent
Wallström

(10) Patent No.: US 6,974,891 B2
(45) Date of Patent: Dec. 13, 2005

(54) ABSORBENT STRUCTURE

(75) Inventor: Leif Wallström, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 65 days.

(21) Appl. No.: 09/732,871

(22) Filed: Dec. 11, 2000

(65) Prior Publication Data

US 2001/0003151 A1 Jun. 7, 2001

Related U.S. Application Data

(63) Continuation of application No. PCT/SE99/00964, filed on Jun. 4, 1999.

(30) Foreign Application Priority Data

Jun. 11, 1998 (SE) .................................... 9802077

(51) Int. Cl.[7] .......................... A61F 13/15; A61F 13/20
(52) U.S. Cl. .......... 604/379; 604/385.01; 604/385.101; 428/213; 428/218
(58) Field of Search ................ 604/358, 365–366, 604/368, 371, 372, 374–384, 385.101, 385.201, 604/385.21, 385.28, 387, 385.01, 385.23; 428/213, 218

(56) References Cited

U.S. PATENT DOCUMENTS

| | | | | |
|---|---|---|---|---|
| 1,974,578 A | * | 9/1934 | Medoff | 604/378 |
| 3,508,548 A | * | 4/1970 | Itochstrasser et al. | 604/380 |
| 3,545,441 A | * | 12/1970 | Graudahl | 604/386 |
| 3,800,797 A | * | 4/1974 | Tunc | 604/364 |
| 3,854,481 A | * | 12/1974 | Messing | 604/386 |
| 3,865,112 A | * | 2/1975 | Roeder | 604/366 |
| 3,906,952 A | * | 9/1975 | Zamist | 604/372 |
| 4,010,752 A | * | 3/1977 | Denny | 604/366 |
| 4,027,672 A | * | 6/1977 | Karami | 604/380 |
| 4,232,674 A | * | 11/1980 | Melican | 604/378 |
| 4,676,784 A | * | 6/1987 | Erdman et al. | 604/368 |
| 4,676,787 A | * | 6/1987 | Sergeant | 604/389 |
| 4,714,466 A | * | 12/1987 | Dohzono et al. | 604/904 |
| 5,047,024 A | * | 9/1991 | Glassman | 604/380 |
| 5,447,506 A | * | 9/1995 | Lindquist | 604/379 |
| 5,741,380 A | * | 4/1998 | Hoyle et al. | 156/62.6 |

FOREIGN PATENT DOCUMENTS

GB 0863582 * 3/1961

* cited by examiner

*Primary Examiner*—Karin Reichle
(74) *Attorney, Agent, or Firm*—Young & Thompson

(57) ABSTRACT

An absorbent structure in an absorbent article such as a diaper, incontinence guard, sanitary napkin, wound dressing, bed protection and the like, formed from at least two superposed layers (5'; 5") of one or more web-shaped absorption materials (5), said layers (5'; 5") having different widths as seen in the transverse direction of the article. The absorbent structure (4) made of said layers has been compressed to a thickness which is substantially the same over the width of the structure, in such a way that the structure has a higher density in the areas thereof where the layers overlap each other and a lower density in other areas.

7 Claims, 2 Drawing Sheets

ABSORBENT STRUCTURE

This application is a continuation of international application PCT/SE99/00964 filed Jun. 4, 1999, which designated the United States, and which was published under PCT Article 21(2) in the English language.

TECHNICAL FIELD

The present invention refers to an absorbent structure in an absorbent article such as a diaper, incontinence guard, sanitary napkin, wound dressing, bed protection and the like, formed from at least two superposed layers of one or more web-shaped absorption materials. The invention further refers to a method for manufacturing the absorbent structure.

BACKGROUND OF THE INVENTION

Many different types of absorbent structures in absorbent articles of the above mentioned kind are previously known. They usually consist of one or more compressed layers of cellulosic fluff pulp, often in combination with superabsorbents, which are polymers with the capacity to absorb water or body liquids many times their own weight. Other types of absorbent structures are airlaid cellulosic fibrous webs which have been bound, with a bonding agent, e.g. latex, heat meltable bonding fibers or the like, dry formed reel pulp, absorbent foam materials etc.

The body liquid is discharged to the absorbent article in a very limited area, the so called wetting point. It shall from there be distributed further to unutilized portions of the absorbent structure. Above all it is desired to have a distribution of liquid in the longitudinal direction of the article, while avoiding spreading toward the longitudinal edges, which can result in edge leakage.

Through EP 0 481 322 there is known an absorbent structure made from a web-shaped absorption material which in its initial position has an even density and thickness in the xy-direction and which has been compressed to a higher density and by that a lower thickness in certain areas. The material is then folded together to form at least two layers which have different densities. In this way an absorbent structure having different densities in the z-direction can be produced.

U.S. Pat. No. 4,027,672 discloses an absorbent body in the form of a pulp structure, in which a pattern of varying basis weights has been created, for example by forming openings in the pulp pad. The pad is then compressed to a substantially uniform thickness, at which the portions having the higher thickness will get a higher density as compared to the portions having the lower density.

U.S. Pat. No. 5,649,916 discloses an absorbent structure comprising three or more superposed absorbent members having an increased wicking capacity along the x- and y-axes relative to the preceding absorbent member. The absorbent members can be in the form of folded web-shaped materials having different widths and different wicking capacities.

OBJECT AND MOST IMPORTANT FEATURES OF THE INVENTION

The object of the present invention is to provide an absorbent structure in an absorbent article of the above mentioned kind, in which it in a simple way is possible to create areas of different densities in the xy-direction of the structure. This has according to the invention been provided by the fact that the structure comprises at least two superposed layers of one or more web-shaped absorption materials, said layers having different widths as seen in the cross direction of the article and that the absorbent structure comprised of said layers has been compressed to a thickness which is substantially the same over the width of the structure, in such a way that the structure has a higher density in the areas thereof where the layers overlap each other and a lower density in other areas.

The layers can either be formed from one and the same web-shaped absorption materials which have been folded to the desired configuration or alternatively be formed from separate pieces of the web-shaped material, which either can be the same in the different layers or different.

The invention further refers to a method for manufacturing an absorbent article, at which at least two layers of one or more web-shaped absorption materials are placed superposed to each other, said layers having different widths as seen in the transverse direction of the article and that the absorbent structure comprised of said layers is compressed to the thickness which is substantially the same over the width of the structure, in such a way that the structure will have a higher density in the areas thereof where the layers overlap each other and a lower density in other areas. Further features of the invention are disclosed in the following description and from the claims.

DESCRIPTION OF THE DRAWINGS

The invention will in the following be closer described with reference to some embodiments shown in the accompanying drawings.

DESCRIPTION OF EMBODIMENTS

Figure 1:
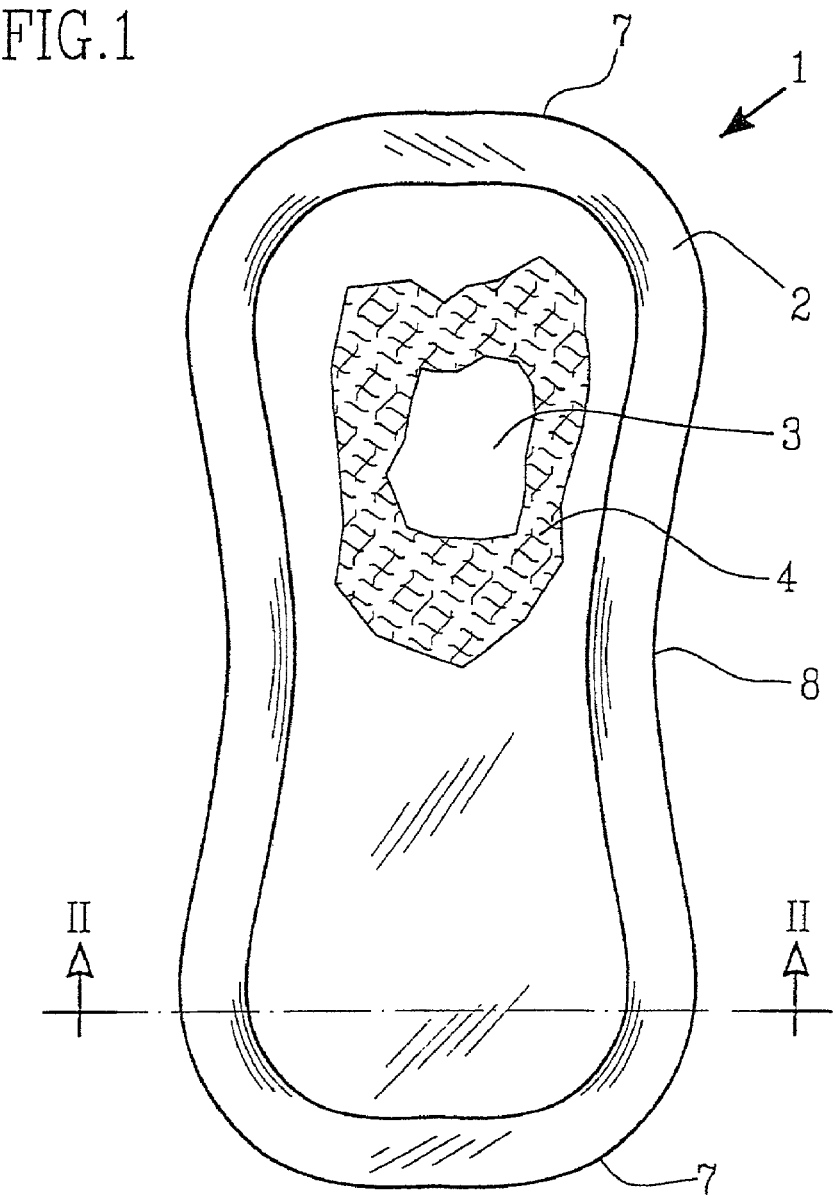
FIG. 1 shows in a partial cutaway view from above an absorbent article in the form of a sanitary napkin.
Figure 2:
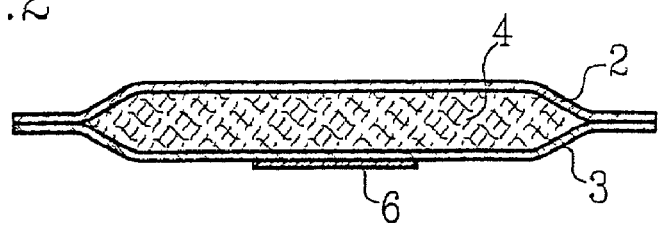
FIG. 2 is a section according to the line II—II in FIG. 1.

FIGS. 1 and 2 shows an embodiment of a sanitary napkin 1 comprising a liquid pervious topsheet 2, a liquid impervious backsheet 3 and an absorbent body 4 arranged therebetween. Further layers be included, such as liquid acquisition layers, distribution layers etc.

It should be pointed out that the sanitary napkin shown in the drawings only constitutes a non-limiting example of an absorbent article. Thus the shape and construction of the article may vary. The absorbent article can also consist of a diaper, a pant diaper, an incontinence guard, a would dressing a bed protection and the like.

The liquid pervious topsheet 2 may consist of a nonwoven material, for example a spunbond material of synthetic filament, a meltblown material, a thermobonded material or a bonded carded fibrous web. Alternatively it may consist of a perforated plastic film or a perforated laminate of nonwoven or plastic film.

The liquid pervious backsheet 3 may consist of a plastic film, a nonwoven material which is coated with a liquid impervious material or a hydrophobic nonwoven material which resists liquid penetration.

On the underside of the liquid impervious backsheet 3 fastening means in the form of one or more longitudinal strings 6 of adhesive glue are provided. The glue areas are preferably before use covered with a releasable protective strip (not shown) of paper or plastic film treated with a release agent. In the shown embodiment the fastening means consist of longitudinal glue areas. A plurality of other glue patterns, e.g. crosswise, are of course possible as well as other types of fastening means such as VELCRO material (hook and loop), press buttons, girdles, special underpants and the like.

The sanitary napkin in the shown embodiments is hourglass shaped with broader end portions 7 and a narrow crotch portion 8. The crotch portion 8 is the portion of the sanitary napkin which during use is intended to be placed in the crotch area of the user and serve as a receiving surface for the discharged body fluid.

The topsheet 2 and the backsheet 3 have a somewhat larger extension in the plane of the absorbent body 4 and extend outside the edges thereof. The layers 2 and 3 are interconnected within the projecting portions, e g by gluing or welding with ultrasonic or heat.

The absorbent body 4 can be of an optional web-shaped absorption material 5, such as airlaid cellulosic fibers which have been bonded with a bonding agent, e g latex, heat meltable bonding fibers or the like, dry-formed reel pulp, sheets of absorbent foam material etc. A certain amount of superabsorbent material may possibly be incorporated in the absorption material.

Figure 3:
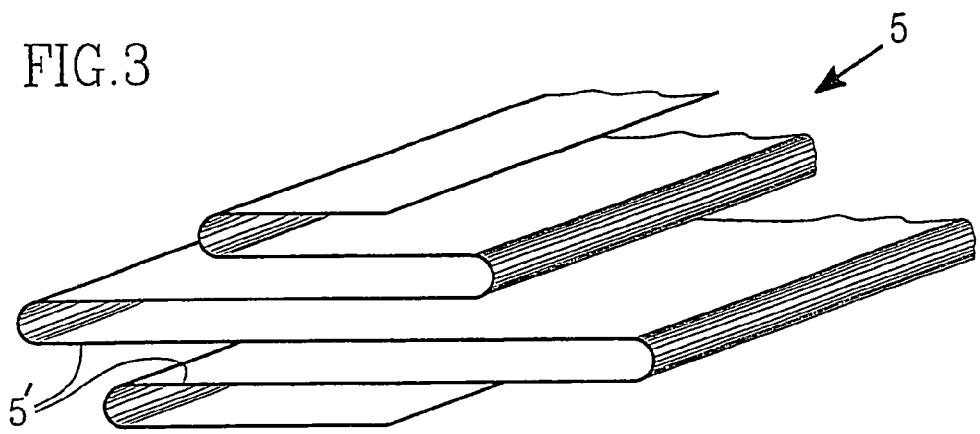
FIG. 3 shows schematically an irregularly folded absorption material forming the start point for an absorbent structure according the invention.

The absorption material 5 according to the embodiment shown in FIG. 3 is irregularly folded in zigzag-shape along five folding lines, in such a way that six layers 5' are formed which have different widths. The outer of these layers 5' have the smallest width while the innermost layers have the largest width. The configuration of the irregular folding can of course be varied in many different ways, of which the shown only is one example. The irregularly folded web-shaped absorption material forms the start point for the production of the absorbent structure according to the invention.

Figure 4:
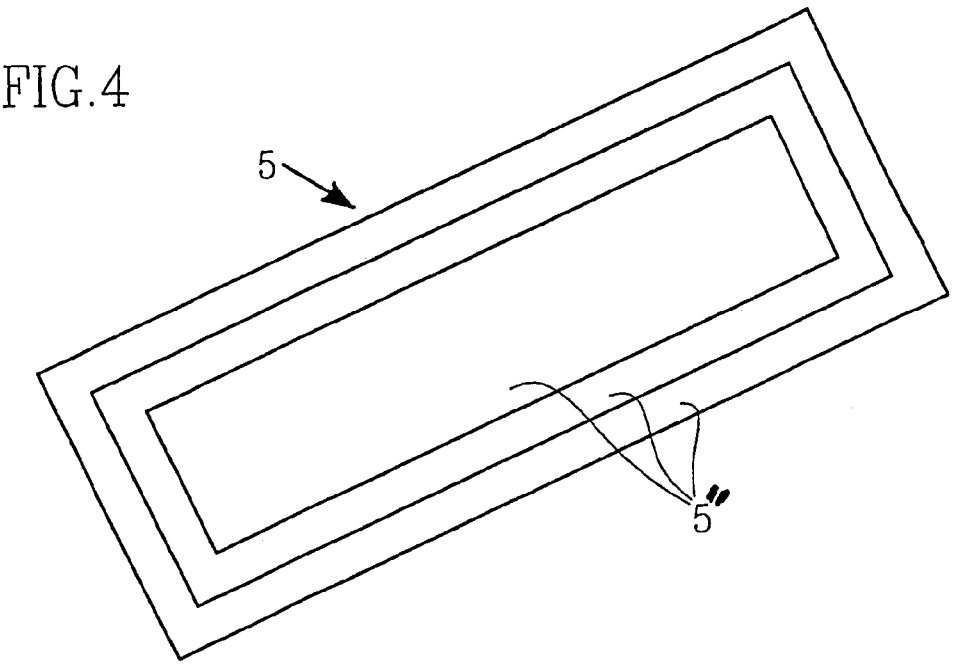
FIG. 4 shows schematically strips of a web-shaped absorption material of different widths placed superposed to each other and forming the start point for an absorbent structure according to the invention.
Figure 5:
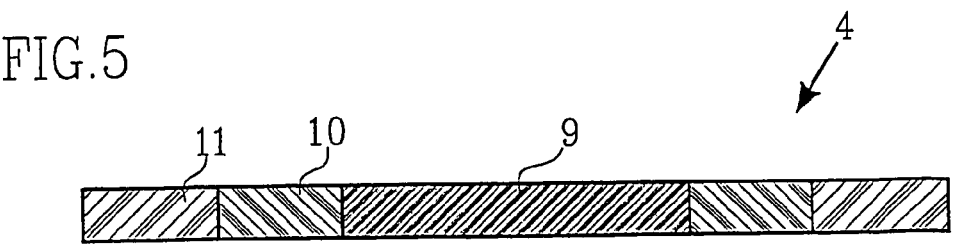
FIG. 5 shows schematically an absorbent structure with different densities in different areas obtained by compressing the material shown in FIG. 3 or FIG. 4.

In the embodiment shown in FIG. 4 three separate strips 5" of a web-shaped absorption material have been placed in superposed relationship. These strips have three different widths and can be of the same or of different web-shaped absorption materials. Besides they have different lengths.

Upon compressing any of the materials composed of several layers according to FIG. 3 or 4 to an even thickness the portions that consist of the most layers will have a density which is higher than that of the portions that consist of fewer layers. In the shown embodiments the middle portion 9 will have the highest density and the immediately outside said middle portion located side portions 10 will have a higher density, while the outermost edge portions 11 will have the lowest density.

Since liquid is more rapidly distributed in smaller capillaries, which means a more rapid distribution with an increased density, the liquid will at first hand be distributed along the hardest compressed middle portion 9, while the outside this located portions 10 and 11 will serve as a kind of safety zones, which mainly are utilized when the middle portion is saturated with liquid. With such a construction of the absorbent article edge leakage from the longitudinal edges of the article can be minimized. If the layers also have different lengths as is shown in FIG. 4, the risk for edge leakage from the transverse edges of the article is also minimized.

The different material layers can be compressed together in a pattern for forming longitudinal compression lines, at which the liquid distribution in the longitudinal direction is further improved.

What is claimed is:

1. An absorbent structure suitable for use in an absorbent article, comprising:
   first, second, and third superposed strips of at least one web-shaped absorption material, said first, second, and third strips being dimensioned and arranged so that a perimeter of the first strip lies entirely inside of a perimeter of the second strip, and a perimeter of the second strip lying entirely inside a perimeter of the third strip;
   the absorbent structure (4) comprised of said strips having been compressed to a thickness which is substantially the same over the structure, so that the structure has a higher density in the area thereof where the strips overlap each other and a lower density in other areas.

2. The absorbent structure according to claim 1, wherein the first, second, and third superposed strips comprise at least two different said web-shaped absorption materials.

3. An absorbent structure suitable for use in an absorbent article, comprising:
   a sheet of web-shaped absorption material (5) which has been folded back and forth upon itself to produce a plurality of effective layers arranged so that a number of the effective layers in a center of the absorbent structure is greater than a number of the effective layers in a peripheral area on each side of the center area, and the folded sheet having been compressed to a thickness which is substantially the same over the structure, so that in cross-section the structure has a higher density in the center area where the effective layers overlap each other and a lower density in the peripheral areas.

4. The absorbent structure according to claim 3, wherein the sheet of web-shaped absorption material is folded in zigzag-shape in such a way that the structure in the center area comprises more of the effective layers than the peripheral areas.

5. An absorbent article comprising:
   an absorbent structure comprising first, second, and third superposed strips of at least one web-shaped absorption material, said first, second, and third strips being dimensioned and arranged so that a perimeter of the first strip lies entirely inside of a perimeter of the second strip, and a perimeter of the second strip lying entirely inside a perimeter of the third strip, the absorbent structure comprised of said strips having been compressed to a thickness which is substantially the same over the structure, so that the structure has a higher density in the area thereof where the strips overlap, each other and a lower density in other areas;
   a liquid pervious topsheet (1), and
   a liquid impervious backsheet (2),
   wherein the absorbent structure is arranged between the topsheet and the backsheet.

6. An absorbent article comprising:
   an absorbent structure comprising a sheet of web-shaped absorption material (5) which has been folded back and forth upon itself to produce a plurality of effective layers arranged so that a number of the effective layers in a center of the absorbent structure is greater than a number of the effective layers in a peripheral area on each side of the center area, and the folded sheet having been compressed to a thickness which is substantially the same over the structure, so that in cross-section the structure has a higher density in the center area where the effective layers overlap each other and a lower density in the peripheral areas;

a liquid pervious topsheet (1), and a liquid impervious backsheet (2), wherein the absorbent structure is arranged between the topsheet and the backsheet.

7. A method for making an absorbent structure in an absorbent article, comprising the steps of:

placing first, second, and third strips of at least one web-shaped absorption material superposed with each other, said first, second, and third strips being dimensioned and arranged so that a perimeter of the first strip lies, entirely inside of a perimeter of the second strip, and a perimeter of the second strip lying entirely inside a perimeter of the third strip; and compressing said strips to form the structure having a thickness which is substantially the same over the structure, so that the structure will obtain a higher density in the area thereof where the strips overlap each other and a lower density in other areas.

* * * * *